(12) United States Patent　　(10) Patent No.:　US 12,665,078 B2
Bauer et al.　　　　　　　　　　(45) Date of Patent:　Jun. 23, 2026

(54) EVENT-DRIVEN SPIKING NEUTRAL NETWORK SYSTEM FOR DETECTION OF PHYSIOLOGICAL CONDITIONS

(71) Applicant: CHENGDU SYNSENSE TECHNOLOGY CO., LTD., Sichuan (CN)

(72) Inventors: Felix Bauer, Zurich (CH); Dylan Muir, Allschwil (CH)

( * ) Notice: Subject to any disclaimer, the term of this patent is extended or adjusted under 35 U.S.C. 154(b) by 1006 days.

(21) Appl. No.: 17/622,471

(22) PCT Filed: Jun. 24, 2020

(86) PCT No.: PCT/EP2020/067755
§ 371 (c)(1),
(2) Date: Dec. 23, 2021

(87) PCT Pub. No.: WO2020/260422
PCT Pub. Date: Dec. 30, 2020

(65) Prior Publication Data
US 2022/0270751 A1　　Aug. 25, 2022

(30) Foreign Application Priority Data
Jun. 24, 2019　(EP) ..................................... 19182041

(51) Int. Cl.
*G16H 40/63*　　　(2018.01)
*G06N 3/004*　　　(2023.01)
*G06N 3/008*　　　(2023.01)

(52) U.S. Cl.
CPC ............. *G16H 40/63* (2018.01); *G06N 3/004* (2013.01); *G06N 3/008* (2013.01)

(58) Field of Classification Search
None
See application file for complete search history.

(56) References Cited

U.S. PATENT DOCUMENTS 5,092,343 A * 3/1992 Spitzer .................. G06N 20/00
706/22
9,993,209 B1 * 6/2018 Fujitani ................. G16H 40/63
(Continued)

FOREIGN PATENT DOCUMENTS

CN　　109906101　　6/2019
EP　　1164537　　12/2001

OTHER PUBLICATIONS

Unsupervised heart-rate estimation in wearables with Liquid states and a probabilistic readout; Das et. al. (Year: 2018).*
(Continued)

*Primary Examiner* — Mandrita Brahmachari
(74) *Attorney, Agent, or Firm* — Michael D. Eisenberg; MDE Patents

(57)　　　　　ABSTRACT

The invention relates to an event-driven spiking neural network system (100) and a method for detecting a physiological condition of a person based on a detected physiological signal of the person, the system comprising at least the following components:

At least one sensor (111-1) configured and arranged to detect a physiological signal and to convert the physiological signal in a sensor signal (112) indicative of the physiological signal, A signal conversion module (120) configured and arranged to receive the sensor signal (112) from the at least one sensor (111-1) and to convert the sensor signal (112) in at least one time series of discrete events, An artificial neuron population (140) comprising a plurality of artificial event-driven spiking neurons (131-1, 131-N) arranged in an event-driven spiking neural network, wherein the neuron population (140) is configured and arranged to receive events, wherein the neuron population (140) is arranged to recognize the physiological condition of the person based on the (Continued)

Method for detecting conditions in biograms
1000 received events, wherein the neuron population (140) is configured to provide one or more processed time series of events to, A condition detection module (150) arranged and configured to receive the events from the neuron population (140) and to output a trigger signal (180), when the events received from the artificial neuron population (140) indicate that the physiological signal comprises a feature indicative of the physiological condition.

10 Claims, 7 Drawing Sheets

(56)                References Cited

U.S. PATENT DOCUMENTS

| | | | | |
|---|---|---|---|---|
| 2008/0114564 A1* | 5/2008 | Ihara | G06F 16/35 | |
| | | | | 702/158 |
| 2014/0114975 A1* | 4/2014 | Rouat | G06N 5/022 | |
| | | | | 707/737 |

| | | | | |
|---|---|---|---|---|
| 2016/0070673 A1* | 3/2016 | Wang | G06F 17/14 | |
| | | | | 708/403 |
| 2016/0210552 A1* | 7/2016 | Kasabov | G06N 3/049 | |
| 2016/0335534 A1* | 11/2016 | Nere | G06N 3/044 | |
| 2018/0137408 A1* | 5/2018 | Mailhot | G06N 3/10 | |
| 2018/0174028 A1* | 6/2018 | Lin | G06N 3/04 | |
| 2018/0174040 A1* | 6/2018 | Davies | G06N 3/084 | |
| 2019/0146849 A1* | 5/2019 | Leonard | G06F 9/542 | |
| | | | | 718/104 |
| 2022/0319651 A1* | 10/2022 | Poeze | A61B 5/7285 | |

OTHER PUBLICATIONS

Anup Das et al, "Unsupervised Heart-rate Estimation in Wearables With Liquid States and a Probabilistic Readout", arxiv.org, Cornell University Library, 201 Olin Library Cornell University Ithaca, NY 14853, Jul. 18, 2017 (Jul. 18, 2017).

Eduardo Ros et al, "Event-Driven Simulation Scheme for Spiking Neural Networks Using Lookup Tables to Characterize Neuronal Dynamics", Neural Computation, vol. 18, No. 12, Oct. 19, 2006 (Oct. 19, 2006), p. 2959-2993.

* cited by examiner

Signal conversion unit
122

Input signal 1220

12211

Tunable bandpass filter 1221

Step value 1224

+ 1225-1

- 1225-2

Reference value 1223

1222-1

1226-1
Event stream 1

1222-2

1226-2
Event stream 2

12212

Input expansion module
130

13-1 Input event stream 1

13-2 Input event stream 2

...

13-N Input event stream N

Event bus 132

133-1

133-2

...

133-M 134-1 Output event stream 1

134-2 Output event stream 2

134-M Output event stream M

Fig. 7

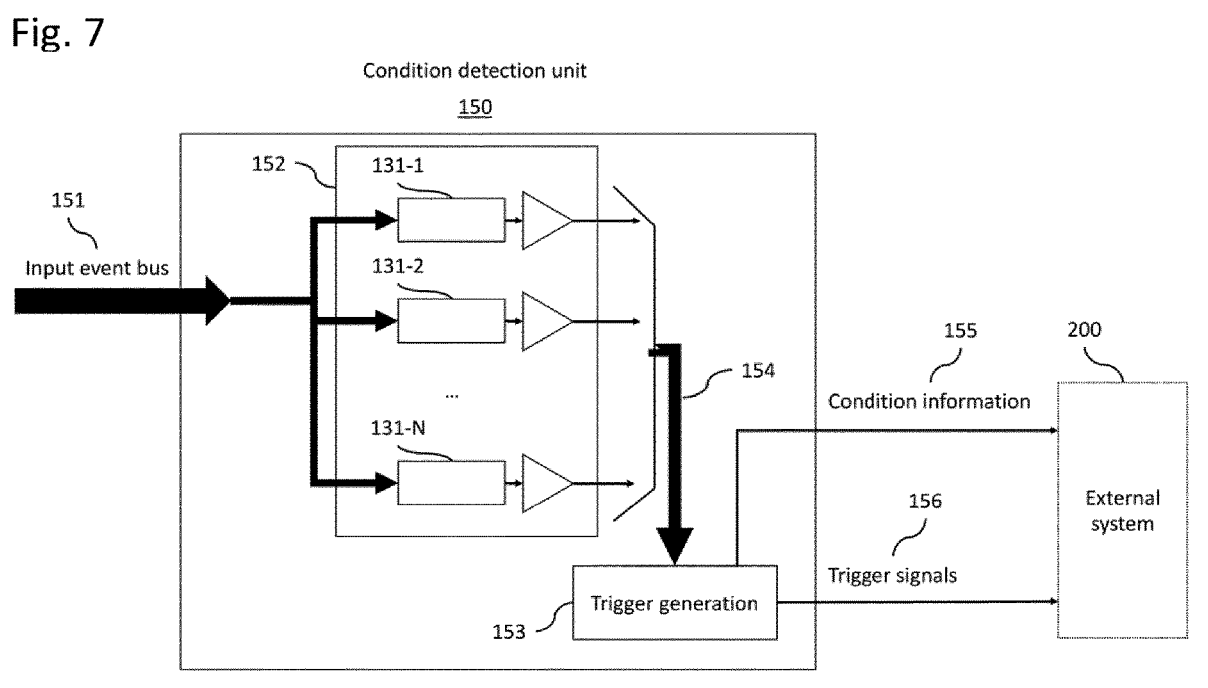

Condition detection unit
150

151

Input event bus

152

131-1

131-2

...

131-N

154

153 Trigger generation

155
Condition information

156
Trigger signals

200

External
system

Method for detecting conditions in biograms
1000

Method for configuring an apparatus for detection of conditions in biograms
<u>1100</u>

EVENT-DRIVEN SPIKING NEUTRAL NETWORK SYSTEM FOR DETECTION OF PHYSIOLOGICAL CONDITIONS

CROSS-REFERENCE TO RELATED APPLICATIONS

This is the U.S. National Stage of International Patent Application No. PCT/EP2020/067755 filed on Jun. 24, 2020, which claims the benefit of European Patent Application No. 19182041.4 filed on Jun. 24, 2019.

The invention relates to an event-driven spiking neural network system for identifying a physiological condition of a person based on a detected physiological signal, as well as to a method for detecting a physiological condition.

Many pathological conditions can be detected by examining measured physiological signals from the subject. For example, pathological heart conditions can be detected by examining the signals caused by electrical activity of the heart of the subject. One or more simultaneous electrical recordings are sometimes used, which can detect the electrical signals used to cause contractions of the heart muscles. Alternatively, optical or other sensors might measure the pressure waves in blood flow through the body, which reflect the contractions of the heart. These sensor signals are collectively referred to as biograms, regardless of the sensors used. A biogram therefore comprises a sensor signal or a plurality of sensor signals.

Examination and diagnosis of a sensor signal (for example, a set of ECG traces) by skilled professionals is important for diagnosing pathological conditions, but is highly time consuming. For this reason, a sensor signal is often recorded only once a pathological issue is suspected, in a doctor's office or hospital. On the other hand, continuous monitoring can potentially detect pathological conditions before they become acutely medically relevant.

Systems for sensor signal analysis known in the art rely on clocked-based computing, often known as von Neumann computing systems. These systems can be implemented as digital signal processors (DSPs), microprocessors or microcontrollers, central processing units or CPUs, graphical processing units or GPUs, or ASICs containing clock-based processing units. Von Neumann processors perform computation physically separate from data and program storage (also referred to as memory). Von Neumann processors therefore must fetch data from memory, fetch program instructions from memory, move the data and instructions to an execution module (or arithmetic logic unit also referred to as "ALU"), perform the requested computation, then move the result back to memory. Moving data and instructions between memory and the ALU incurs severe time and energy costs.

The authors Das et al, "Unsupervised Heart-rate Estimation in Wearables With Liquid States and A Probabilistic Readout", ARXIV.org, CORNELL UNIVERSITY LIBRARY, 201 OLIN LIBRARY CORNELL UNIVERSITY ITHACA, N.Y. 14853, 18 Jul. 2017 (2017-07-18), XP081279151, 001:10.1 016/J.NEUNET.2017.12.015 disclose a system for detecting heart beats of a person, wherein said system comprises a sensor, a spike encoder for encoding the detected heartbeats of the sensor into a stream of spike events, as well as a spiking neuronal network that is configured to detect heart beats in the stream of events. However, the technology employed in this paper does not allow for a more detailed analysis of the physiological signal, such as a determination of a shape of the heart beat signal or other features of the signal indicative of a physiological condition, as spike encoding is based on a synchronized, clock-based system. This in turn however, does not allow reconstructing the original signal from the sensor, which means that a more detailed analysis of the sensor signal cannot be performed due to the loss of information associated with the clock-based approach. A determination of a physiological condition that requires more information and a deeper analysis of the sensor signal is therefore impossible by said system.

An object of the present invention is to provide a system that overcomes the drawbacks of von Neumann processors and provide a device for analysis of physiological signals.

An event-driven spiking neural network system for detecting, and particularly identifying a physiological condition of a person based on a detected physiological signal, particularly for identifying a pathological condition in photoplethysmogram signals recorded from the person, comprises at least the following components:

at least one sensor configured and arranged to detect a physiological signal such as a vascular activity, such as heart beats, a heart rate or a heart rate variability, and convert the physiological signal in a particularly electric sensor signal indicative of the physiological signal, a signal conversion module configured and arranged to receive the sensor signal from the at least one sensor and to particularly asynchronously convert the sensor signal in at least one time series of discrete particularly binary events, particularly by means of Lebesgue sampling the sensor signal and/or a function of the sensor signal, such as a derivative thereof, particularly wherein each event is indicative of a change of the sensor signal, such as an increase or a decrease of the sensor signal, and/or an exceeding or falling below of a threshold value, an artificial neuron population comprising a plurality of artificial event-driven spiking neurons arranged in an event-driven spiking neural network, wherein the neuron population is configured and arranged to receive events, particularly one or more time series of events, wherein the neuron population is arranged, particularly trained to recognize the physiological condition of the person based on the received events, wherein the neuron population is configured to provide one or more processed time series of events to, A condition detection module arranged and configured to receive the events, particularly the one or more time series of events particularly via an output bus from the neuron population and particularly trained to output a trigger signal, when the events, particularly the one or more processed time series of events indicate that at least one of the detected physiological signal comprises a feature indicative of the physiological condition.

In contrast to von Neumann based computation, the system according to the invention takes a distributed memory approach, particularly as each neuron in the neuron population is an elementary computation and memory unit.

Computation and memory are therefore physically distributed across the network system, which particularly minimizes the time and energy costs associated with processing data.

In addition, the system according to the invention is particularly configured to perform pipelined processing, wherein events from the time series are progressively moved through a computational pipeline, particularly comprising the neuron population, wherein with each computational component, i.e. neuron, repeatedly performing the same computation but on different events. As a result, the time and energy costs associated with fetching instructions are minimized.

It is noted that particularly each component or module is a hardware component, particularly specifically configured for the task associated with said component or module.

This system according to the invention further allows for a continuous real-time monitoring and integrated local analysis of sensor signals while offering very low power consumption as compared to von Neumann systems and a compact size, such that it is compatible with an implementation in low-power wearable devices.

The term "event-driven" particularly refers to the system being configured to process events and information not in clocked-synchronized fashion but on an event-per-event basis, i.e. when an event is provided to a component of the system, said component will start processing the event, and particularly output an event, independent of a global synchronizing clock for synchronizing the components of the system.

This allows for an accurate reconstruction of the information comprised in the signal of the at least one sensor and therefore an analysis of the signal beyond the sole detection of the signal with regard to a physiological condition that might be detectable in the signal.

The term "event-driven" in the context of the current specification therefore particularly relates to an asynchronous generation and processing of events, particularly independent of a clock cycle used by a synchronized event-generating module.

The term "asynchronous" particularly refers to a processing scheme of the system that is devoid of any clock-based or cycle-based processing. Any incoming signal, for example from a sensor is converted by the signal conversion module into an event, wherein a time associated to the event generation by the signal conversion module is not clocked or cycled by a timer.

As a consequence, from the time series of events that might be generated by the signal conversion module it is possible to encode the complete information of the signal into the stream of events. In a clock-based system, predefined event spacing in the stream does not allow to encode the complete information of the signal form the sensor.

According to another embodiment of the invention, the signal conversion module converts the signal of the at least one sensor such that a complete information of the signal is encoded in the stream of events.

Particularly, the signal conversion module is configured to generate events in an asynchronous fashion.

According to another embodiment of the invention, the signal conversion module is an asynchronously-operating module, such that event-generation is fully asynchronous.

According to another embodiment of the invention, the artificial neuron population and the condition detection module are configured to process events in an asynchronous fashion.

According to another embodiment of the invention, the artificial neuron population and the condition detection module are asynchronously-operating components of the system. According to another embodiment of the invention, all components comprised by the system are configured to process events in an asynchronous fashion.

According to another embodiment of the invention, all components of the system are asynchronously-operating components of the system.

Particularly if no event is received by a component, said component remains inactive until an event is received.

The term "physiological condition" particularly refers to a condition that exhibits particularly unique properties being indicative to a physiological state of the person.

Thus, the physiological condition might by indeed a pathological condition such as a heart attack but also non-pathological conditions such as physical exertion during work-out.

Particularly, a feature indicative of a physiological condition comprises a shape information, a frequency information of the signal, an amplitude or any combination thereof, particularly wherein the feature indicative of the physiological condition relies on the complete information of the signal of the at least one sensor.

The sensor signal can comprise a photoplethysmogram signal recorded from the person, but also an EEG signal, a cardiogram or other signals detected at the person.

The at least one sensor outputs a sensor signal that is indicative for the physiological signal. Such output signals can for example be a digital voltage signal coding for the physiological signal or an analog voltage signal being essentially proportional to the physiological signal.

The sensor can for example be at least one of:
an accelerometer;
an inertial measurement unit (IMU);
an optical sensor, such as a photoplethysmograph;
an EEG.

The signal conversion module may include computational elements that are configured to compute a summation or a difference of the at least one sensor signal. Particularly, the signal conversion module comprises one or more signal conversion units that are configured to each receive a sensor signal particularly from a plurality of sensors and convert the sensor signal(s) in a plurality of time series of events.

The signal conversion module, particularly each signal conversion unit may be configured to convert the sensor signal into one or more time series of events, particularly wherein the time series of events is generated by detecting increases or decreases in the sensor signal, and wherein each time an increase or a decrease in the sensor signal is detected an events is generated by the conversion module particularly the conversion unit.

Each signal conversion unit may further include a tunable bandpass filter for filtering the sensor signal prior to conversion to events, i.e. the conversion is based on a function of the sensor signal.

The term "Lebesgue sampling" particularly refers to a non-uniform, particularly non-periodic sampling scheme for signals, in which the sampling times depend on the sensor signal to be sampled. Lebesgue sampling is a signal level-triggered sampling method, characterised in that the sensor signal is sampled every time it crosses one of a plurality of predefined signal levels. Therefore, information of the signal is encoded in the frequency of events generated, more precisely in the time intervals between events.

The sampled, i.e. converted sensor signal is particularly a binary signal, which reduces transmission bandwidth.

The neurons comprised in the artificial neuron population are event-driven neurons and are also referred to as neuron devices in the context of the specification.

Each neuron may receive the events from the at least one time series of events via an event bus comprised by the system.

Particularly in case a plurality of time series of events is received by the artificial neuron population, each neuron may further comprise a list of addresses that is indicative of which events, particularly which time series is to be processed by said neuron, i.e. which events may alter a neuron state of the neuron. The neuron state of the neuron is particularly an event-driven value stored in the neuron, but can be an continuously updated analog or digital value as well.

Each address of the list may be associated with information on whether the events of the time series have a positive or negative effect on the neuron, particularly on the neuron state, in terms of increasing or decreasing the chance that the neuron emits an event, i.e. increasing or decreasing the neuron state, and particularly the strength of the effect the event has on the neuron, i.e. to what extend the chance of emitting an event is increased or decreased, i.e. how much the neuron state is altered in response to the event.

A neuron comprised in the artificial neuron population may further implement a summation of events received, and when a threshold condition is satisfied, may emit an output event. This summation alters the neuron state.

The event-driven artificial neuron population comprises a plurality of event-driven neurons, wherein the neurons are configured in a connectivity network also referred to as event-driven spiking neural network in the context of the specification. The connectivity network may include connections within and between neurons in the event-driven neuron population.

According to another embodiment of the invention, the event-driven artificial neuron population is connected to an input bus and configured to receive the events from the at least one time series of events via said input bus.

Further, according to another embodiment of the invention, the artificial neuron population is connected to an output bus and configured to send events generated by the neurons via said event output bus, particularly wherein the processed time series is sent via said output bus.

According to yet another embodiment of the invention, the artificial neuron population is inter-connected with an internal bus and configured to send and distribute generated events via said internal bus.

Particularly the internal bus serves as to provide the neuron population with a recurrent network configuration.

Alternatively, according to another embodiment of the invention, the input, internal and/or the output busses are comprised in a single bus and sharing the said single bus.

Busses and time series of events may be implemented in several ways. For example, each time series of event may be implemented as an independent signal pathway.

Alternatively, each time series may be associated with an address to be signaled on the bus, which then acts as a shared bus. The bus may then be implemented as a multiplexed data bus, with other devices listening for appropriate addresses on the multiplexed bus.

According to another embodiment of the invention, the neuron population recognizes a physiological condition by producing a dynamic state comprising a plurality of events that allow the condition detection module to detect, particularly to decide whether the physiological signal comprises the feature indicative of the physiological condition.

The condition detection module may include one or more neurons, each of which is associated with the detection of a particular physiological condition in the sensor signal or the sensor signals.

These physiological conditions may signal the presence of pathological or nominal medical states, or signal the presence of other states of interest as elaborated previously.

The trigger signal sent by the condition detection module particularly indicates the detection and characteristics of a detected physiological condition, to an external system.

The trigger signal is particularly designed to signal the occurrence of a detected physiological condition to an external system.

According to another embodiment of the invention, the event-driven spiking neural network system comprises an event-driven signal expansion module comprising at least a first layer of event-driven spiking artificial neurons, wherein the signal expansion module is configured and arranged to receive the events particularly the at least one time series of events from the signal conversion module and to generate from each event, particularly from each incoming time series of events e.g. from different sensors, a plurality of outgoing events, particularly a plurality of outgoing time series of events by means of the first layer of neurons processing the incoming events, and particularly provide the plurality of outgoing events or time series of events to the artificial neuron population.

The term "layer" particularly refers to at least one electronic circuit that represents a layer in an artificial neural network as understood by the person skilled in the art.

According to another embodiment of the invention, the expansion module is configured to process events in an asynchronous fashion.

According to another embodiment of the invention, the expansion module is an asynchronously-operating component of the system.

The event-driven signal expansion module may process one or a plurality of time series of events received from the conversion module and compose these into a plurality of outgoing time series. The plurality of time series is particularly sent to the artificial neuron population via the input bus. At the artificial neuron population the events, particularly the time series of events are routed, particularly by means of the address list to the neurons for further processing as elaborated previously.

Thus, events comprised in a selected time series of events may be made available to one or more event-driven neurons, particularly by means of the address list.

Each event-driven neuron may generate an event or a time series of events that can be combined into the processed time series.

According to another embodiment of the invention, the first layer of neurons in the signal expansion module is arranged and configured in a feed-forward configuration only.

According to this embodiment, processing of events takes place in a strictly feed forward fashion, i.e. events processed by the first layer are not feedback to the first layer but provided to the artificial neuron population. As such the first layer is not configured as a recurrent layer.

According to another embodiment of the invention, the artificial neuron population is arranged as a recurrent neural network, particularly as a purely recurrent network, particularly wherein the neurons in the neuron population are arranged in a second layer, particularly in only one second layer of artificial neurons.

This embodiment provides an efficient network structure to the system.

According to another embodiment of the invention, the condition detection module comprises a third layer of artificial neurons, particularly wherein the third layer is arranged and configured in a feed-forward configuration only.

The third layer is particularly required for the operation of the system, such that the system is configured to selectively recognise physiological states.

According to another embodiment of the invention, the third layer is trained to detect the physiological condition from the events received form the artificial neuron population, particularly from the plurality of processed time series of events.

According to another embodiment of the invention, the system comprises a plurality of sensors for detecting physiological signals providing a plurality of sensors signals to the signal conversion module, particularly wherein each sensor is configured and arranged to detect a physiological signal different from the physiological signals that the remaining sensors of the plurality of sensors are configured and arranged to detect.

This embodiment allows monitoring a plurality of physiological signals acquired from the person, which renders the system more sensitive and robust for physiological condition detection.

Moreover, this embodiment allows for multiple types of analysis that be performed simultaneously. E.g. gait recognition from inertial sensors, while at the same time performing heart-beat analysis from a PPG sensor.

Particularly if one sensor malfunctions, the system according this embodiment is still operational due to the redundancy provided by the signals detected by the remaining sensors.

According to another embodiment of the invention, the system is configured to identify a plurality of physiological conditions from the at least one detected physiological signal.

This embodiment allows for broad variety of applications. Particularly, according to this embodiment the artificial neuron population comprises a plurality of neuron units, each unit being trained to process the events or time series of events for a different physiological condition.

According to another embodiment of the invention, the signal conversion module, the signal expansion module, the artificial neuron population and/or the condition detection module are comprised in single, particularly wearable, particularly battery-driven device.

This embodiment provides a compact device allowing for the detection of physiological conditions.

According to another embodiment of the invention, the at least one sensor is an optical sensor configured to generate a plethysmogram signal from the vascular activity of the person.

Optical sensors provide non-invasive detection capabilities and reliably monitor physiological signals such as the heart rate or a pulse.

According to another embodiment of the invention, particularly the signal conversion module comprises a conversion module input bus configured and arranged to transmit the sensor signals from the at least one sensor to the signal conversion module, particularly wherein the conversion module input bus connects the sensor with the conversion module, wherein for each sensor signal received by the conversion module the signal conversion module generates two time series of events, particularly wherein a first time series of the two time series of events is indicative that the sensor signal has increased and wherein a second time series of the two time series of events is indicative that the sensor signal has decreased, wherein the signal conversion module is configured and arranged to provide the at least two time series of events to the signal expansion module and/or to the artificial neuron population.

According to another embodiment of the invention, the neurons of the neuron population comprises an input bus for events, wherein the input bus is connected to an event filter comprised by each neuron, wherein the event filter is configured to update the neuron state of the neuron for selected events received from the input bus, wherein the neuron further comprises an event generator configured to generate an event, when the neuron state of the neuron exceeds or falls below a predefined threshold value.

Some embodiments and features of the input bus have been elaborated in previous embodiments in the specification.

The event filter particularly comprises the address list, such that a selection of events of the time series that are to be processed by said neuron is achieved.

For example, in case the event filter identifies an event that is to processed by the neuron, said event particularly alters the neuron state. The event generator monitors the neuron state of the neuron and in case the altered neuron state exceeds or falls below a predefined or trained threshold value the event generator generates an event. Said event is then processed further either by other neurons in the neuron population (e.g. internal bus routing) or send to the condition detection module (e.g. output bus routing).

According to another embodiment of the invention, each neuron of the neuron population comprises a balancer configured and arranged to adjust an output frequency of events of the neuron based on a frequency of incoming events leading to an update of the neuron state and/or based on a cumulative effect of incoming events on the neuron state, leading to an update of the neuron state.

This allows the system to become more robust and prevent neuron activity overflow.

According to another embodiment of the invention, the condition detection module comprises a trigger unit configured to generate the trigger signal, and wherein trigger unit is configured to provide information about the detected physiological condition such as to provide an identification of the detected physiological condition.

According to another embodiment of the invention, the system is connected or connectable to an external particularly computerized system, wherein the condition detection module is configured to provide the trigger signal to the external system.

Such external computerized system might include a smart device, such as a smart watch, a central computer of a medical facility, such as a hospital.

Particularly wherein the central computer is configured to inform medical personal in case a trigger signal is received about the physiological condition.

According to another embodiment of the invention, the system comprises a signal storage configured to store the sensor signal from the at least one sensor respectively the sensor signals from the plurality of sensor signals, wherein upon detection of a physiological condition, a portion of the sensor signal indicative of the physiological condition is provided to the external system.

This embodiment allows a skilled person to reassess the sensor signal portion(s) e.g. for verification of the detected physiological condition.

The signal storage is particularly configured as a recording buffer and may hold a record of at least a portion of the sensor signal(s). This buffer may be constantly updated, such that it always contains a record of the most recent portion of sensor signal(s) over some predefined period of time. The recording buffer may further be queried by the external system, to return the currently recorded sensor signal(s). Alternatively, the recording buffer may be controlled by the condition detection module to send the currently recorded sensor signal(s) to the external system. The term "computerized system" or a similar term denotes an apparatus comprising one or more processors operable or operating according to one or more programs.

While the system according to the invention generally relates to an event-driven neuronal system, said system can be connected to ordinary computerized systems or computer.

Where applicable, the term 'computer', or system thereof, are used herein as ordinary context of the art, such as a general purpose processor or a micro-processor, RISC processor, or DSP, possibly comprising additional elements such as memory or communication ports, particularly when such computer is an external device of the system. Optionally or additionally, the term 'computer' or derivatives thereof denote an apparatus that is capable of carrying out a provided or an incorporated program and/or is capable of controlling and/or accessing data storage apparatus and/or other apparatus such as input and output ports. The term 'computer' denotes also a plurality of processors or computers connected, and/or linked and/or otherwise communicating, possibly sharing one or more other resources such as a memory.

The problem according to the invention is furthermore solved by a method for detecting a physiological condition from a physiological signal, particularly using the system according to the invention, the method comprising the steps of: Providing a physiological signal, particularly generated by a simulation or recorded with the at least one sensor from a person, the sensor generating a sensor signal indicative of the physiological signal, Converting the sensor signal in at least one time series of discrete events, particularly by means of a Lebuesgue transformation, with the signal conversion module, Providing the at least one time series of events to the neuron population, At the neuron population processing the events from the at least one time series in an event-driven fashion, wherein at least one processed time series is generated by the artificial neuron population, Providing the events of the processed time series to the condition detection module, At the condition detection module generating a trigger signal, when the physiological condition is detected from the processed time series, Providing the trigger signal to an external system such as to inform about the detected physiological condition.

The method according to the invention can be a computer-implement method

Terms and definitions of features disclosed and defined for the system according to the invention apply in a corresponding fashion to the method and vice versa.

The method and the system can be implemented at least in part a smart device, such as a smart watch. The method then may alert the person wearing the smart device, cause storage of the sensor signals, i.e. the sensors signal(s) particularly the portions comprising the detected physiological condition, and/or collect and/or display statistics of the detected physiological condition.

The method and the system can also be implemented at least in part in a wearable device for health care of patients in a medical facility: the method then may raise a medical alert, and/or send the sensor signal to a health practitioner for diagnosis. Furthermore, the method might store the sensor signal for later diagnosis, and collect statistics of the physiological condition.

According to another embodiment of the method, the method further comprises the steps of: Providing the at least one time series generated by the conversion module to the signal expansion module, At the signal expansion module generating for each received time series of events a plurality of time series of events and providing said plurality of time series to the neuron population.

According to yet another embodiment of the method, the method further comprises the steps of: Recording the at least one sensor signal and if the physiological condition is detected, Providing at least a portion of the at least one sensor signal to the external system, the sequence comprising the sensor signal portion being indicative of the detected physiological condition.

The problem is furthermore solved by a computer program, comprising computer program code that when executed on a computerized device causes the device to execute the computer-implementable method steps.

FIGURE DESCRIPTION AND EXEMPLARY EMBODIMENTS

Particularly, exemplary embodiments are described below in conjunction with the Figures.

FIG. 7 shows a schematic drawing of a condition detection module;

Figure 1:
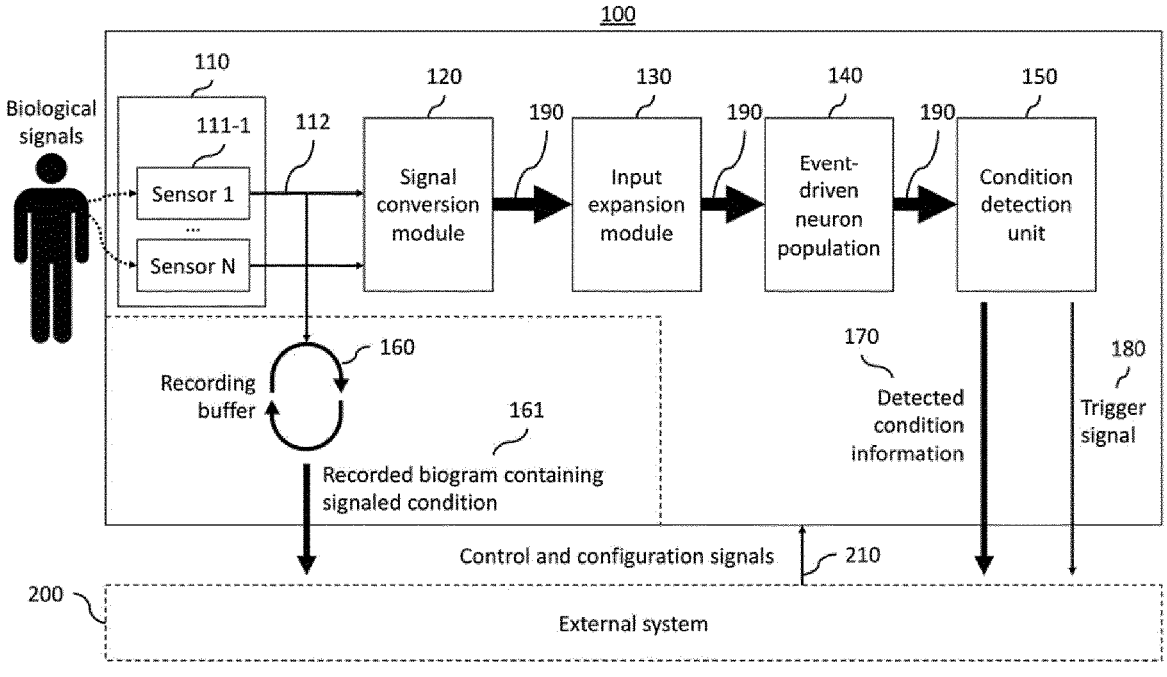
FIG. 1 shows a schematic drawing of an event-driven spiking neural network system according to the invention, and its interactions with an external system.

FIG. 1 schematically illustrates event-driven spiking neural network system 100 for detecting pathological or other conditions in physiological signals. The physiological signals are detected by one or more sensors that convert the detected physiological signals in sensor signals, these sensor signals are also collectively referred to as biograms.

The system 100 comprises a biological signal sensing unit 110, a signal conversion module 120, a signal expansion module 130, an event-driven artificial neuron population 140, a condition detection module 150, and a recording buffer 160.

The system 100 is configured to communicate with an external system 200, by sending information 170 about a detected condition, and/or by sending one or more trigger signals that indicate that a physiological condition has been detected 180. The system 100 may also transfer a recorded biogram (i.e. a recorded sensor signal) 161 or a portion thereof to the external system 200.

The external system 200 may send control and configuration signals 210 to control the operation of the system 100, for example to cause the transmission of a recorded sensor signal 161 or a portion thereof.

The biological signal sensing unit 110 may contain a number of sensors 111-1 . . . 111-N, also referred to as sensing devices in the context of the specification. Each of these sensing devices 111 detects some physiological signal, for example electrical voltage changes caused by the heart beat (commonly known as "ECGs" or "EKGs"), or blood oxygenation levels.

Each sensing device 111 may send the sensor signal (particular yin form of an electrical waveform signal) 112 to the signal conversion module 120, and may also send a copy of the sensor signal 112 to a signal storage, that might be formed as a recording buffer 160.

Figure 2:
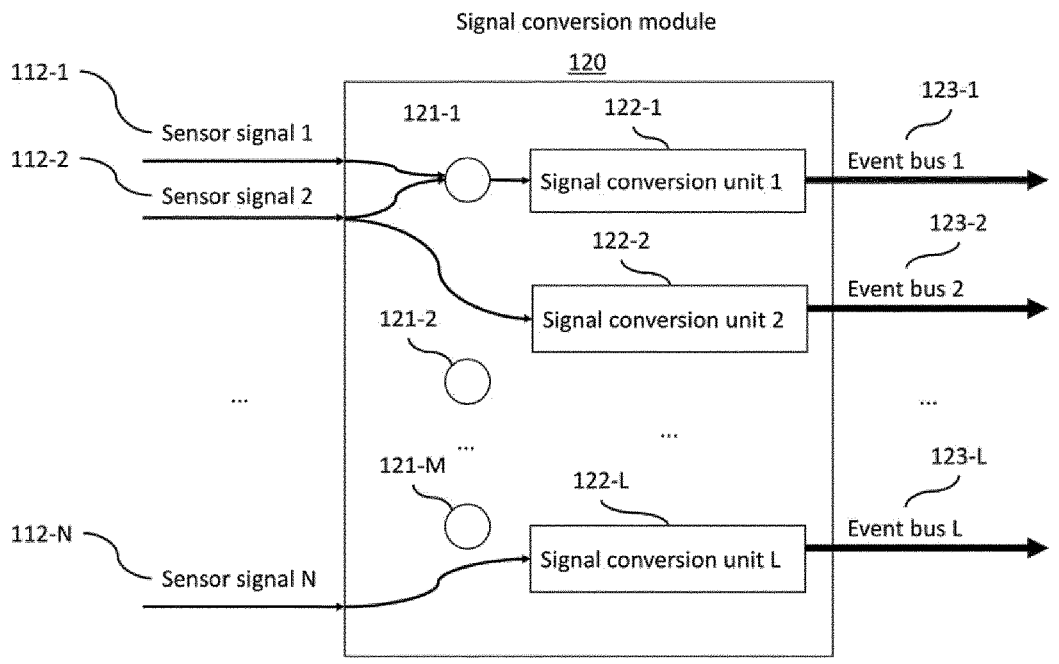
FIG. 2 shows a schematic drawing of a signal conversion module.

FIG. 2 illustrates a schematic embodiment of the signal conversion module 120.

The signal conversion module 120 may receive sensor signals 112-1 . . . 112-N from the sensors 111-1 . . . 111-N.

The signal conversion module 120 may further include a number of signal combination units 121-1 . . . 121-M, which are configured to compute summations or differences between two or more sensor signals 112.

The signal conversion module 120 may further include a number of signal conversion units 122-1 . . . 122-L, which convert the received sensors signal(s) into one or more time series of binary digital events. The time series of events is a digital signal assuming only binary values. A time series of events is also referred to as an event stream.

Each signal conversion unit may output a series of event streams as an event bus 122-1 . . . 122-L.

The signal conversion module 120 may alternatively be implemented without signal combination units 121-1 . . . 121-M, or with the option to bypass the signal combination units.

Figure 3:
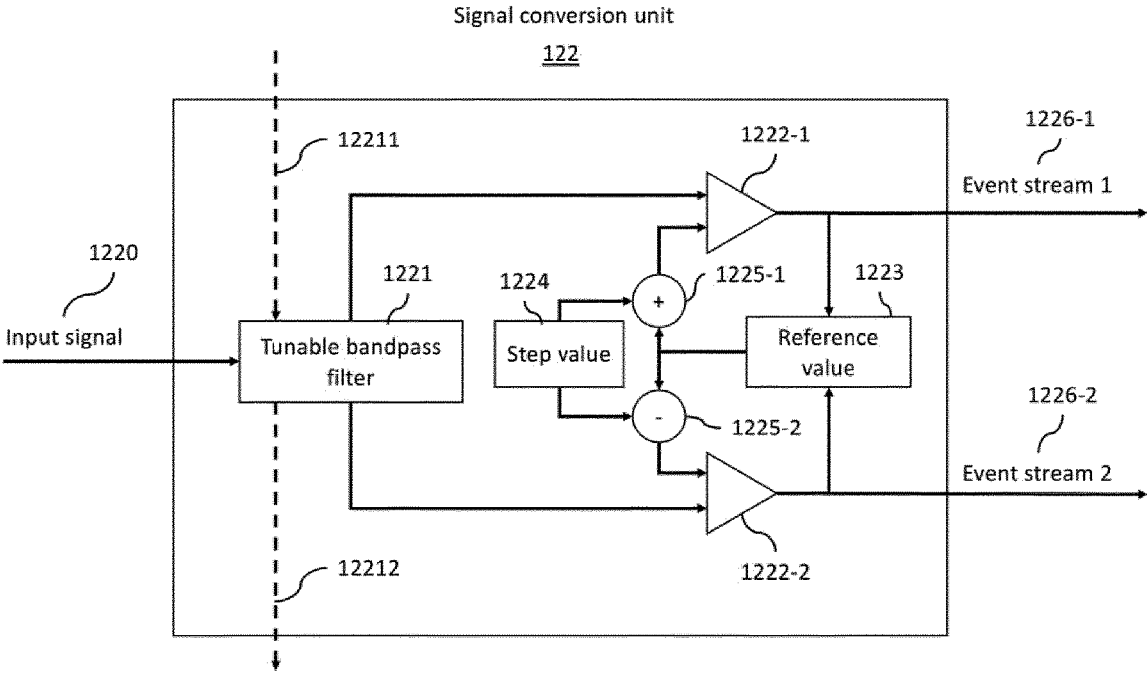
FIG. 3 shows a schematic drawing of a signal conversion unit.

FIG. 3 illustrates one embodiment of the signal conversion unit 122.

The signal conversion unit comprised by the conversion module 120 may receive an input signal 1220, that can be a sensor signal processed by a combination unit 121-1 . . . 121-M or an unprocessed sensor signal 112-1, . . . 112-N. The input signal, like the sensor signal may be an analogue waveform, e.g. an analogue voltage signal.

The signal conversion unit 122 may further contain a tunable bandpass filter 1221, which may amplify or suppress particular frequency bands of the input signal 1220. In another embodiment the bandpass filter may be bypassed, in which case it does not modify the input signal 1220. In yet another implementation, the bandpass filters from adjacent signal conversion units may be connected using signals 12211 and 12212, to facilitate filtering of the input signals 1220.

The signal conversion unit 122 may further include comparators 1222-1 and 1222-2, which may signal when the input signal 1220 is above or below a threshold value.

The signal conversion unit 122 may further include a device 1223 that maintains a reference value for comparison. The reference value 1223 is compared against the current value output by the bandpass filter 1221, with the addition or subtraction of a step value 1224. The step value 1224 is combined with the signal from the bandpass filter 1221 by addition 1225-1 or subtraction 1225-2.

One comparator 1222-1 may therefore operate by detecting when the filtered input signal 1221 increases above the current reference value 1223 by a fixed step 1224.

The comparator may respond by generating and emitting an event into a first event stream 1226-1. When the comparator 1222-1 emits an event, the reference value 1223 may increase its stored value by the step value 1224.

Similarly, the other comparator unit 1222-2 may operate by detecting when the filtered input signal 1221 decreases below the current reference value 1223 by a fixed step 1224. The comparator may respond by generating and emitting an event into a second event stream 1225-2.

When the comparator 1222-2 emits an event, the reference value 1223 may decrease its stored value by the step value 1222.

An event in the first event stream 1225-1 may therefore signal an increase in the filtered input signal. Likewise, an event in the second event stream 1225-2 may therefore signal a decrease in the filtered input signal.

In another embodiment, the comparators 1222-1 and 1222-2 may each be connected to independent step values 1224.

In another embodiment, the comparators 1222-1 and 1222-2 may be replaced by a device with a leaky integrator, such that events are generated and emitted when the integrated filtered signal 1221 passes a threshold.

Figure 4:
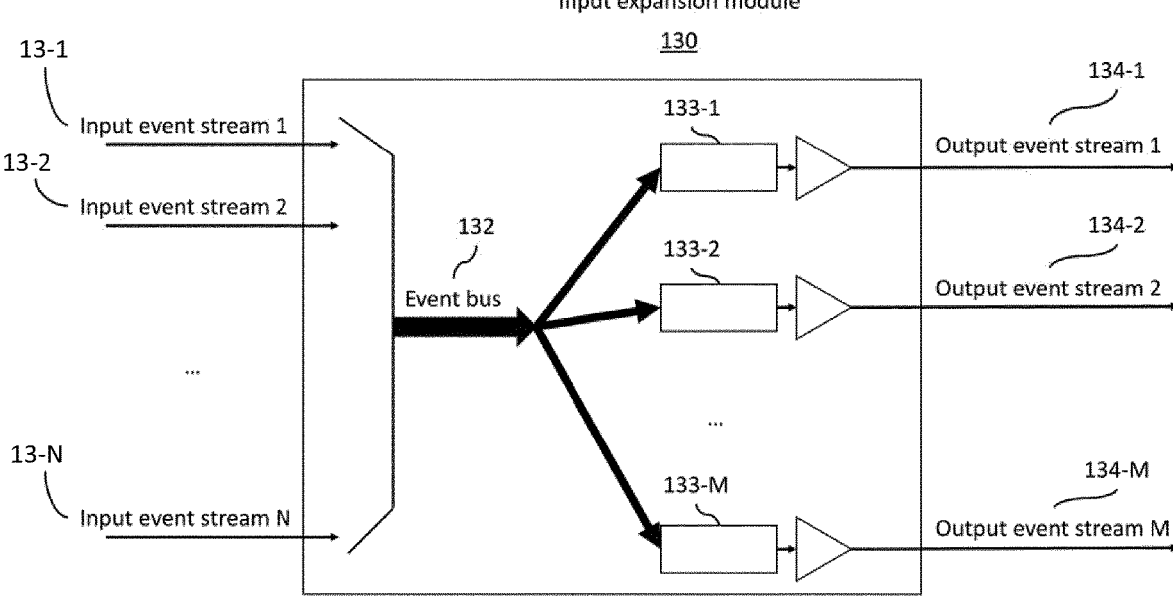
FIG. 4 shows a schematic drawing of a signal expansion module.

FIG. 4 illustrates an embodiment of the signal expansion module 130.

The signal expansion module 130 may receive a number of input event streams 13-1 . . . 13-N, also referred to as incoming time series of events that are combined into an event bus 132 which comprises all the input event streams.

The signal expansion module 130 may further include a number of event-driven neurons also referred to as neuron devices 133-1 . . . 133-M, each of which receives input from the event bus 132, and each of which may produce an output event stream 133-1 . . . 133-M also referred to as outgoing time series of events in the current specification.

Figure 5:
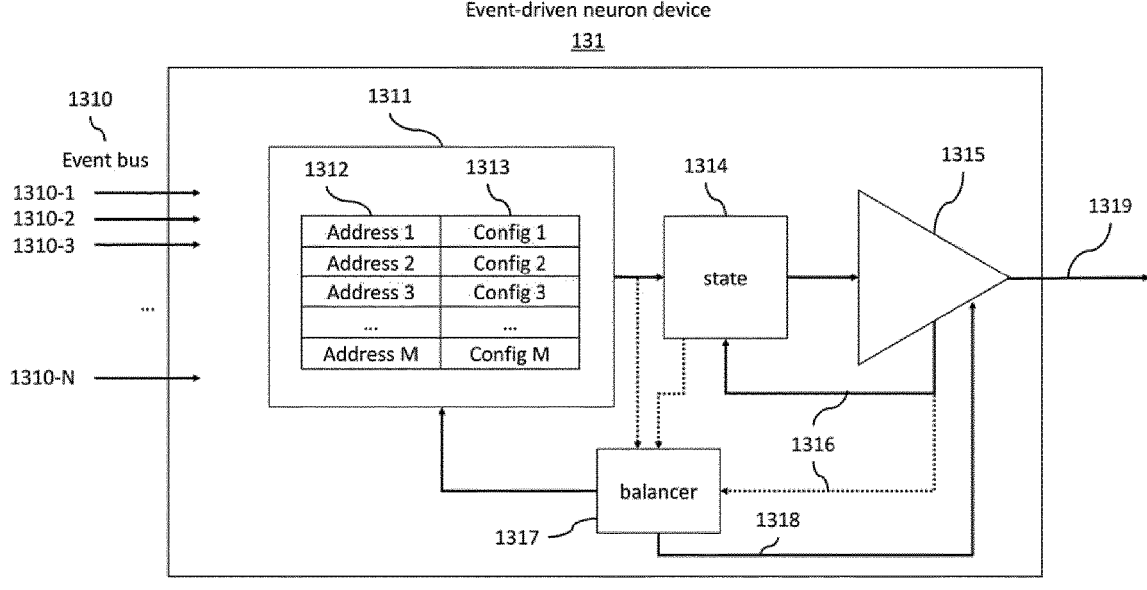
FIG. 5 shows a schematic drawing of a neuron.

FIG. 5 illustrates an embodiment of an event-driven neuron device 131.

The event-driven neuron device 131 may receive as input an event bus 1310, which may comprise several event streams 1310-1 . . . 1310-N.

The event-driven neuron device 131 may further comprise a configurable event filter 1311; a state unit 1314 which maintains the current state of the neuron; a spike generation unit 1315; and a balancer unit 1317.

The configurable event filter 1311 may contain a list of addresses 1312 (comprising addresses 1312-1 . . . 1312-M). The configurable event filter may further contain a list of address associated configurations 1313, numbered 1313-1 . . . 1313-M, with each being associated to an address comprised in the address list 1312. The list of addresses 1312 may hold addresses corresponding to event streams in the event bus 1310.

The configurable event filter 1311 may continually monitor the event bus 1310.

When an event occurs on an event stream, matching an address 1312-1 . . . 1312-M comprised by the address list 1312, the event filter 1311 updates the current state of the neuron 1314. If the address matches an event, then the corresponding associated configuration is used.

The used configuration may cause the event filter 1311 to update the neuron state 1314 in a variety of ways. For example, the event filter may simply instantly add or subtract a specified value from the neuron state. In another embodiment, the event filter 1311 may cause the addition or subtraction of a value that changes over time, according to a predefined temporal function. In another embodiment, the event filter 1311 may add or subtract a value proportional to the current neuron state 1314.

The neuron state 1314 may be implemented in a variety of ways. In one embodiment, the neuron state consists of a stored analog or digital value. In another embodiment, the neuron state 1314 may decrease over time through continual subtraction or multiplication by a small number. Similarly, the neuron state 1314 may increase over time.

An event-driven neuron may further include an event generation unit 1315. The event generation unit may generate and emit an event when the current state of the neuron 1314 passes a predefined threshold. It may emit an event into an output event stream 1318. In one implementation, an output event 1316 may also modify the current neuron state 1314.

For example, it may cause a reset of the current state to a predefined value. In another embodiment, an output event 1316 may cause a subtraction of the neuron state 1314 by a predefined value.

In another embodiment, an event-driven neuron 131 may be configured such that once an output event 1316 is emitted, the neuron is prevented from emitting a further output event for a period of time, known as the "refractory period".

The event-driven neuron may further include a balancer 1317. The balancer unit may receive events from the event generation unit 1315, and modify the operation of the event filter 1311. In one embodiment, the balancer 1317 may modify the configurations in the configuration list 1313. For example, the balancer may cause a weakening or strengthening of the values used to modify the neuron state 1314.

In another embodiment, the balancer 1317 may send a signal 1318 to the event generation unit 1315, to modify its action. For example, the balancer 1317 may raise or lower the threshold value used by the event generation unit 1315 to emit an event, or modify the refractory period of the neuron.

The balancer 1317 may operate by counting the output events 1316, and attempting to ensure the rate of output events remains constant on average. In another embodiment, the balancer may operate by monitoring the neuron state 1314, and attempting to ensure the neuron state remains constant on average. In another embodiment, the balancer 1317 may monitor the event filter 1311, and attempt to ensure the total effect of the event filter on the neuron state 1314 remains constant on average. In another embodiment the balancer may ensure the output of the event filter remains constant on average.

Figure 6:
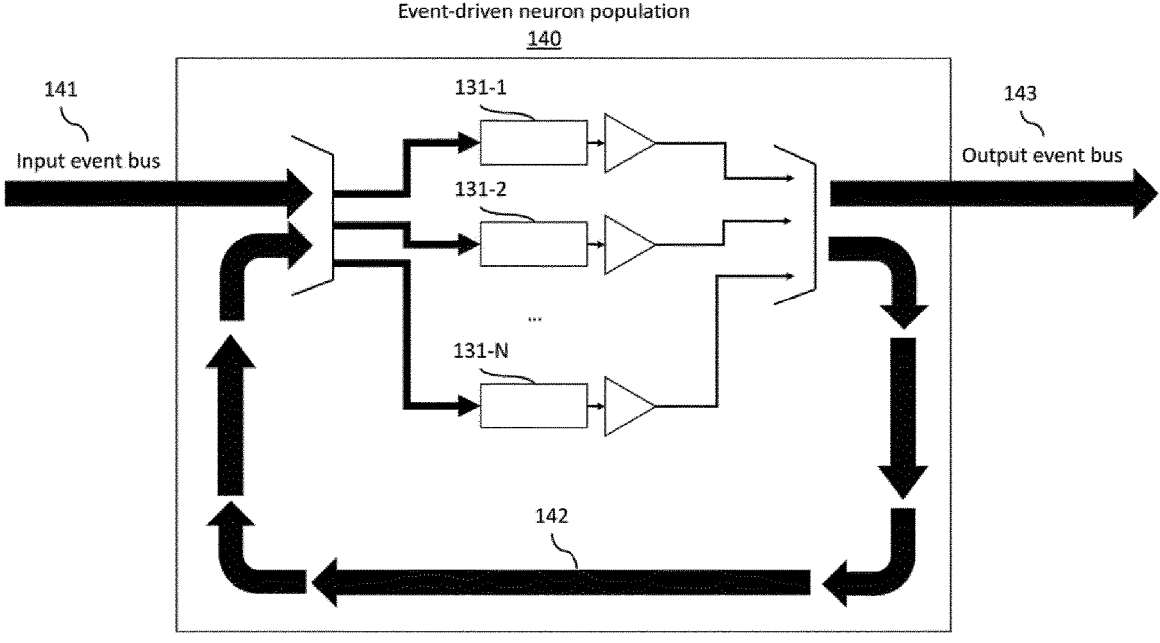
FIG. 6 shows a schematic drawing of an event-driven neuron population.

FIG. 6 illustrates an embodiment of the event-driven neuron population 140.

The event-driven neuron population 140 may consist of an input bus 141 for events, also referred to as input event bus, a number of event-driven neuron devices 131-1 . . . 131-N, an internal bus 142 for events, also referred to as internal event bus and an output bus 143 for events, also referred to as output event bus.

Embodiments of the event-driven neuron devices 131 have been elaborated in previous paragraphs.

Event-driven neurons 131 may receive input events from the input event bus 141, and send output events to the output event bus 143. Event-driven neurons 131 may also copy their output events to the internal event bus 142. The neurons 131 may also receive input from the internal event bus 142, such that the neuron population 131 may respond to events from other units in the population.

FIG. 7 illustrates an embodiment of the condition detection module 150.

The condition detection module may consist of an input event bus 151; a set 152 of event-driven neuron devices 131-1 . . . 131-N, with each neuron device numbered 131-1 . . . 131-N; a trigger generation unit 153; an internal event bus 154; an output bus that is configured to carry information about a detected condition 155; and an output bus that is configured to carry trigger signals 156. The condition detection module may further be configured to communicate with an external system 200.

The set 152 of event-driven neuron devices receives input events from the input event bus 151, and sends output events to the internal event bus 154. The set of neurons may be configured such that each neuron corresponds to a condition in the input sensor signals 112 (cf. e.g. FIG. 2). Under such an embodiment, events from each neuron would indicate that the corresponding condition has been detected in the input sensor signals 112.

In another embodiment, multiple neurons in 152 may correspond to one condition in the input sensor signals 112. Under such an embodiment, events from said multiple neurons would indicate that the corresponding condition has been detected.

In another embodiment, neurons in 152 may correspond to one condition in the input sensor signals 152, but may signal evidence either for or against the detection of the condition. Under such an embodiment, events from said multiple neurons may indicate positive evidence for detection of the corresponding condition; and events from other neurons may signal evidence against the detection of the corresponding condition.

In another embodiment, neurons in 152 may be arranged in several "layers" consisting of one or more neurons each, with connections within and between layers. In this implementation the output of the final layer may emit events on the internal event bus 154.

The condition detection module 150 may further include a trigger generation unit 153.

A trigger generation unit may receive input from the internal event bus 154, and generate signals indicating information about a detected condition 155, as well as a trigger signal 156.

The trigger generation unit 153 may operate by waiting for events on the internal event bus 154 that signal the detection of a condition in the input sensor signals 112. When a condition is detected, the trigger generation unit 154 may send a trigger signal to the external system 200, for example by raising or lowering the voltage of a signal line. The trigger generation unit may also send information about the detected condition over the condition information bus 155 to an external system 200.

The trigger generation unit 153 may send a trigger as soon as one of the event-driven neuron devices 152 emits an event. In another embodiment, the trigger detection unit may integrate events from the neurons 152 until a pre-defined threshold for detection is reached, and then send a trigger signal. In another embodiment, the trigger generation unit 153 may perform a temporal filtering of the events on the internal event bus 154, before integration. In another embodiment, the trigger generation unit 153 may collect evidence for and against detection of a condition signaled by the event-driven neuron devices in the set 152.

In another embodiment, the trigger generation unit 153 may maintain a value for each possible condition indicating the current weight of evidence in favor of detecting that condition. In this embodiment, the trigger generation unit may send a trigger signal 156 when the highest value for a condition is sufficiently higher than for all other conditions, e.g. 10 times higher. In another embodiment, an operation such as a soft-max may be performed over the set of condition values before evaluating a threshold for generating a trigger signal.

The trigger generation unit 153 may further send condition information 155 to the external system 200. In one embodiment, the condition information may consist of information about an identity of the detected condition. In another embodiment, the condition information may include the strength of evidence for the detected condition. In one embodiment, the condition information 155 may only be signaled when a trigger signal 156 is generated.

In another embodiment, the condition information 155 may continually signal which condition currently has the highest amount of evidence.

In one embodiment, a mathematical operation such as a maximum, or a softmax operation over the evidence values, may be used by the trigger generation unit 153 to select the condition with most evidence. In another embodiment, the current evidence for all conditions may be sent to the external system 200.

In one embodiment of the system according to the invention 100, the system may be implemented by a single custom-design silicon chip, particularly except the external system that might reside somewhere else. In another embodiment, the system 100 may be implemented by a number of separate electronic components, with various subsystems of the system implemented separately. For example, the sensors 111-1 and particularly the sensor unit 110 may be implemented separately from the remainder of the system 100. In another example, the sensor signal storage, e.g. the recording buffer 160 may be implemented separately from the remainder of the system. In another implementation, portions of the system 100 may be simulated by a computing system such as a CPU or GPU or similar.

Figure 8:
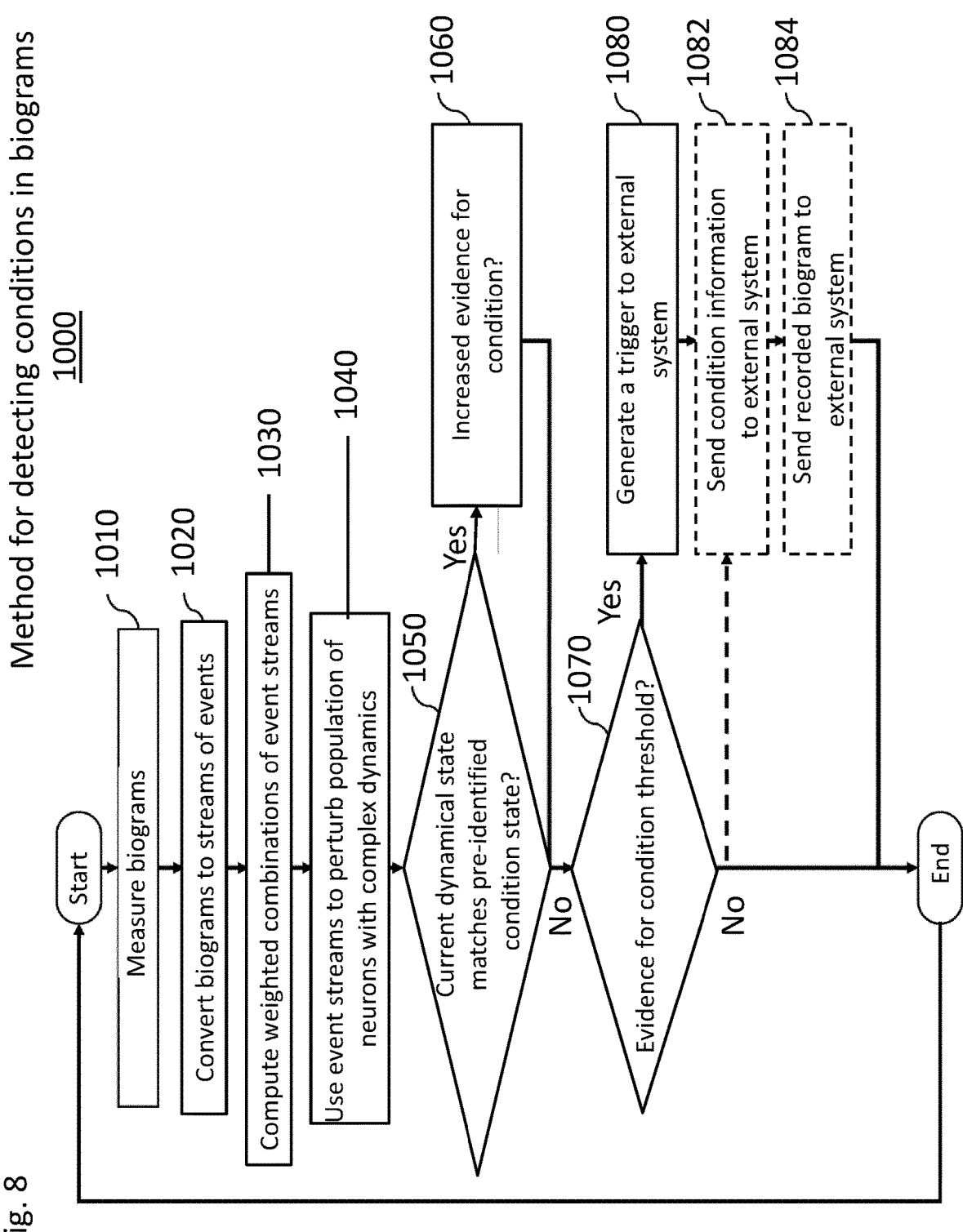
FIG. 8 shows a flowchart for the method for detecting pathological or other physiological conditions in a recorded sensor signal.

FIG. 8 illustrates a method 1000 for detecting a physiological condition in a sensor signal, using the system 100 according to the invention.

In operation 1010, and referring to FIG. 1, at least one sensor 111-1 particularly comprised in the sensing unit 110 generates a sensor signal 112 indicative for the detected physiological signal, and sends the signal to the signal conversion module 120.

In operation 1020, and referring to FIG. 2, the signal conversion module 120 converts the sensor signal 112 into a set of events 123 encoding the sensor signal. These encoded events are sent to the signal expansion module 130.

In operation 1030, and referring to FIG. 4, the events encoding the sensor signal may be weighted and combined by the signal expansion module 130. The neurons 133 in the signal expansion module particularly perform a range of non-linear combinations of the input events, i.e. the events provided from the conversion module, and increase the number and complexity of the event streams between the input events 131 and output events 134, i.e. events generated by the signal expansion module. The output events 134 are sent to the event-driven neuron population 140.

It is noted that throughout the specification, the term "input" combined terms such as "input event" particularly refer to a received input, a received event, or received stream of events, with respect to the corresponding component, e.g. module, unit etc.

It is further noted that throughout the specification, the term "output" combined terms such as "output event" particularly refer to an output, a sent event, or a sent stream of events, with respect to the corresponding component, e.g. module, unit etc.

Therefore, an output event of a first device might serve as the input event for a subsequent device or in a recurrent network architecture even as an input for the same device.

In operation 1040, the event-driven neuron population 140 may receive output events from the signal expansion module 130. As elaborated in the paragraph above, the received output events are referred to input events with respect to the neuron population. The event-driven neuron population 140 may be configured such that it responds to input events with complex patterns of events that persist for some time. This ongoing activity may then be perturbed by newly received input events at the neuron population, such that the dynamic state of the neuron population 140 is a complex combination between instantaneous and past input. The output events 143 produced by the event-driven neuron population are sent to the condition detection module as input events 151.

In operation 1050, the dynamic state of the event-driven neuron population 140 is monitored by the condition detection module 150. Referring to FIG. 7, neurons in the condition detection module respond to events 154 when the instantaneous dynamic state of the event-driven neuron population 140 matches a pre-configured state. Within the condition detection module 150, events 154 are taken to imply evidence for or against the detection of a particular condition in the input sensor signals 112.

Within the trigger generation unit 153, under operation 1060, the evidence for detecting each physiological condition is stored and integrated.

In operation 1070, and again referring to FIG. 7, the trigger generation unit may test whether sufficient evidence is present in favor of a condition. If the evidence in favor of a physiological condition surpasses a predefined threshold, then under operation 1080, a trigger signal may be generated and sent to the external system 200.

In operation 1082, information about the current physiological condition is sent to the external system 200. In one embodiment, generation of a trigger signal in operation 1080 may also cause the physiological condition information to be transmitted. In another embodiment, condition information may be transmitted continuously, intermittently or upon request from the external system 200.

In operation 1084, and referring to FIG. 1, a recording buffer 160 may be used to transmit a set of recorded sensor signals 161 to an external system 200. In one implementation, generation of a trigger signal in operation 1080 may cause a recorded sensor signal 161 or a portion thereof to be transmitted to an external system 200. In another embodiment, transmission of the recorded sensor signal 161 may be under the control of the external system 200.

The method 1000 shown in FIG. 8 is particularly designed to be executed continuously and repeatedly.

Figure 9:
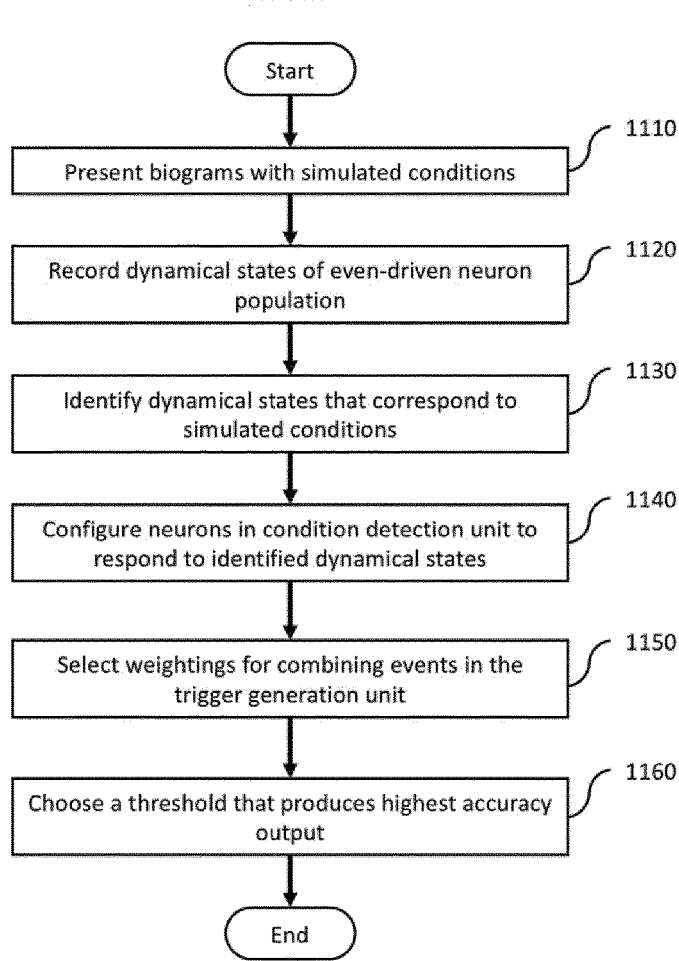
FIG. 9 shows a method for configuring the event-driven spiking neural network system.

FIG. 9 illustrates a method 1100 for configuring a system 100 according to the invention.

In operation 1110, particularly in reference to FIG. 1, at least one simulated or pre-recorded sensor signal may be presented to the system 100, in place of detected sensor signals 112. In another embodiment or alternatively, particularly in reference to FIG. 2, time series of events may be presented in place of output event busses 123 from the signal conversion module 120.

In operation 1120, particularly in reference to FIG. 6, the events produced by the event-driven neuron population 140 may be collected.

In operation 1130, for each physiological condition that is desired to be detected, the patterns of events collected in operation 1120 are grouped according to which physiological condition they correspond, such as to identify the dynamic states of the event-driven neuron population 140 that correspond to a physiological condition.

In one embodiment of operation 1130, a single dynamic state may be selected for and associated to each physiological condition that is to be detected. This can occur for example by computing the average dynamic state over all dynamical stat collected for a given physiological condition.

Alternatively, other mathematical operations could be used to select a dynamic state, for example a median or other operation.

In another embodiment of operation 1130, several dynamic states may be selected for each condition that is desired to be detected. This could be performed for example by executing a clustering analysis of dynamic states collected for a single condition, and choosing some number of clusters as representative dynamic states.

In another embodiment of operation 1130, and particularly in addition to the embodiments described in previous paragraphs, dynamic states may be selected which correspond to the absence of any or all of the physiological conditions that are to be detected. This may be performed for example by using a "maximum margin" classifier to identify dynamic states, or by the techniques described in previous paragraphs of the specification.

In operation 1140, and in reference to FIG. 7, a configuration is chosen for the neurons 152 such that each neuron emits events upon detection of a dynamic state selected in operation 1130. Under the embodiments for operation 1130, one or several neurons 150 may correspond to a single physiological condition that is to be detected. In some embodiments, configurations may be chosen for the neurons 152 such that selected neurons emit events when evidence against the physiological condition is present. These configurations may be chosen, for example, by setting the address list and configuration list for each neuron that is a linear scaling of a chosen dynamic state. In another embodiment, a technique such as a linear or non-linear regression technique may be used to determine the weighting in the configuration list. In yet another embodiment, positive and negative weights may be considered separately for the configuration list. In another embodiment, weights may be chosen by performing a maximum-margin optimization technique or similar.

In operation 1150, particularly referring again to FIG. 7, a set of weights may be selected to combine the events emitted by the neurons 152, such that a value is produced by the trigger generation unit 153 for each physiological condition that is to be detected, such that increasing values indicate increasing evidence for the detection of the corresponding physiological condition. This operation 1150 can be performed by a linear or non-linear regression technique, or by another optimization technique.

In operation 1160, a threshold is chosen for the trigger generation unit 150, to signal the detection of the physiological condition. This may be a single threshold for all physiological conditions, or may be an individual threshold for each physiological condition. These thresholds may be chosen, for example, by evaluating the behavior of the entire system 100 under simulated sensor signals, and searching for a threshold on the evidence values within the trigger generation unit 153 such that true detections and true rejections are maximized, and false positives and misses are minimized.

Figure 10:
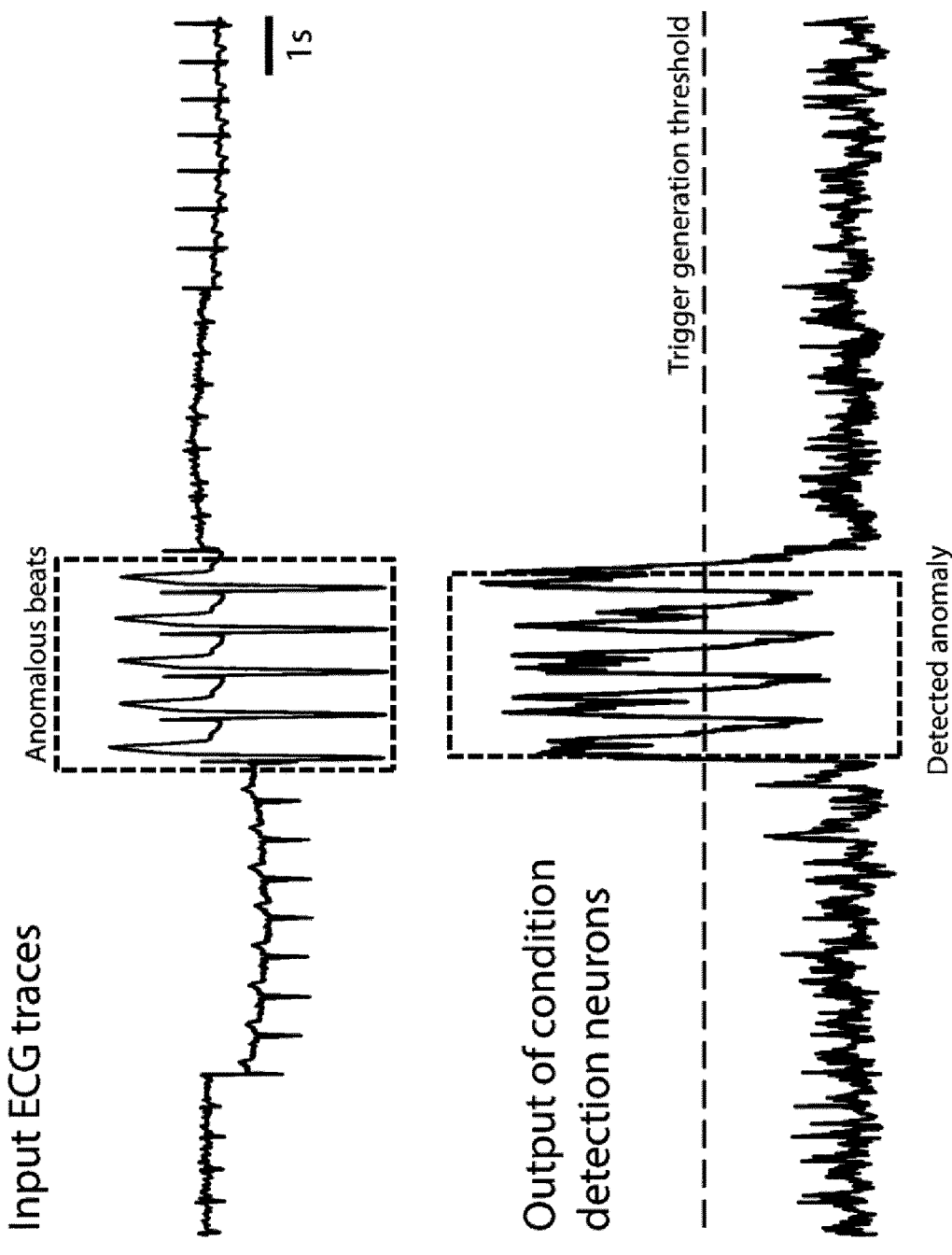
FIG. 10 shows sensor signals and the detection of a physiological condition.

FIG. 10 shows a working example of a system according to the invention. In the upper panel of FIG. 10 a sequence of several seconds of a detected sensors signal in form of ECG traces as detected by an ECG sensor system are shown. After the ECG signal is processed by the signal conversion module, the input expansion module, and the event-driven neuron population, at the condition detection unit the neurons in the condition detection unit exhibit a sequence of strong spikes (lower panel, gray box labelled "detected anomaly") that is indicative of an anomaly in the ECG trace, and thus a physiological condition. The corresponding sequence in the sensor signal is also indicated by a corresponding boxed region (labelled "anomalous beats") above the second panel. As the output of the neurons in the condition detection unit exceeds a trigger generation threshold (dotted line in lower panel) a signal indicative that a physiological condition has been detected is issued by the condition detection unit. This signal then can serve for alarm or information purposes for an external system.

The invention claimed is:

1. An event-driven spiking neural network system implemented on a chip for detecting a physiological condition of a person based on a detected physiological signal of the person, comprising at least the following components:

a plurality of sensors, wherein each sensor is configured and arranged to detect a physiological signal and to convert the physiological signal in a sensor signal indicative of the physiological signal, a plurality of signal conversion modules, wherein each is configured and arranged to receive one or more of the sensor signals from the plurality of sensors and to convert the sensor signals in at least one time series of discrete events by means of a Lebesgue transformation, wherein the generation of events is independent of a global synchronizing clock for synchronizing the components of the system, wherein foreach sensor signal received by the conversion module the signal conversion module generates at least two time series of events, wherein a first time series of events is indicative that the sensor signal has increased and wherein a second time series of the at least two time series of events is indicative that the sensor signal has decreased, wherein the signal conversion module is configured and arranged to provide the at least two time series of events to an event-driven signal expansion module and/or to an artificial neuron population, an event-driven signal expansion module comprising at least a first layer of event-driven spiking artificial neurons, wherein the signal expansion module is configured and arranged to receive the at least one time series of events from the signal conversion module and to generate from each time series of events a plurality of outgoing time series of discrete events by means of the first layer of neurons and provide the plurality of outgoing time series to an artificial neuron population, the artificial neuron population comprising a plurality of artificial event-driven spiking neurons arranged in an event-driven spiking neural network, wherein the neuron population is configured and arranged to receive the time series of discrete events, wherein the neuron population is arranged to recognize the physiological condition of the person based on the received events, wherein the neuron population is configured to provide one or more processed time series of events to, a conditional detection module arranged and configured to receive the events from the neuron population and to output a trigger signal, when the events received from the artificial neuron population indicate that the physiological signal comprises a feature indicative of the physiological condition.

2. The event-driven spiking neural network system implemented on a chip according to claim 1, wherein the first layer of neurons in the signal expansion module is arranged and configured in a feed-forward configuration only.

3. The event-driven spiking neural network system implemented on a chip according to claim 2, wherein the neuron population is arranged as a recurrent neural network, wherein the neurons in the neuron population are arranged in a second layer.

4. The event-driven spiking neural network system implemented on a chip according to claim 1, wherein the condition detection module comprises a third layer of artificial neurons, wherein the third layer is arranged and configured in a feed-forward configuration only, wherein the third layer is trained to detect the physiological condition from the one or more processed time series of events.

5. The event-driven spiking neural network system implemented on a chip according to claim 1, wherein the system comprises the plurality of sensors configured and arranged to detect physiological signals providing a plurality of sensors signals to the signal conversion module, wherein the plurality of sensors is configured and arranged to detect a physiological signal different from the physiological signals that the remaining sensors of the plurality of sensors are configured and arranged to detect.

6. The event-driven spiking neural network system implemented on a chip according to claim 1, wherein the system is configured to identify a plurality of physiological conditions from the at least one detected physiological signal.

7. The event-driven spiking neural network system implemented on a chip according to claim 1, wherein the neurons comprise an input bus for events, wherein the input bus is connected to an event filter comprised by each neuron, wherein the event filter is configured to update a neuron state of the neuron for selected events received from the input bus, wherein the neuron further comprises an event generator configured to generate an event, when the neuron state of the neuron exceeds or falls below a predefined threshold value.

8. The event-driven spiking neural network system implemented on a chip according to claim 7, wherein each neuron of the neuron population comprises a balancer configured and arranged to adjust an output frequency of events of the neuron based on a frequency of incoming events leading to an update of the neuron state and/or based on a cumulative effect of incoming events on the neuron state, leading to an update of the neuron state.

9. The event-driven spiking neural network system implemented on a chip according to claim 1, wherein the system is connected or connectable to an external computerized system, wherein the condition detection module is configured to provide the trigger signal to the external system.

10. The event-driven spiking neural network system implemented on a chip according to claim 9, wherein the system comprises a signal storage configured to store the sensor signal from the at least one sensor, wherein upon detection of a physiological condition, at least a portion of the sensor signal indicative of the physiological condition is provided to the external system.

*    *    *    *    *